(12) United States Patent
Lu et al.

(10) Patent No.: US 8,921,615 B2
(45) Date of Patent: Dec. 30, 2014

(54) PROCESS FOR PREPARING XANTHOPHYLL CRYSTAL

(75) Inventors: Qingguo Lu, Hebei Province (CN); Yunhe Lian, Hebei Province (CN); Xuehui Su, Hebei Province (CN); Xiaodong An, Hebei Province (CN); Yuanxin Cheng, Hebei Province (CN); Lijun Qi, Hebei Province (CN)

(73) Assignee: Chenguang Biotech Group Co. Ltd., Hebei Province (CN)

( * ) Notice: Subject to any disclaimer, the term of this patent is extended or adjusted under 35 U.S.C. 154(b) by 0 days.

(21) Appl. No.: 13/825,772

(22) PCT Filed: Dec. 31, 2011

(86) PCT No.: PCT/CN2011/002235
§ 371 (c)(1),
(2), (4) Date: Aug. 26, 2013

(87) PCT Pub. No.: WO2013/097056
PCT Pub. Date: Jul. 4, 2013

(65) Prior Publication Data
US 2014/0303406 A1 Oct. 9, 2014

(51) Int. Cl.
*C07C 35/21* (2006.01)

(52) U.S. Cl.
CPC ..................... *C07C 35/21* (2013.01)
USPC .......................... 568/816; 568/834

(58) Field of Classification Search
None
See application file for complete search history.

(56) References Cited

U.S. PATENT DOCUMENTS

| 5,648,564 | A | 7/1997 | Ausich et al. | |
|---|---|---|---|---|
| 6,743,953 | B2 | 6/2004 | Kumar et al. | |
| 7,150,890 | B2 | 12/2006 | Rosales et al. | |
| 7,271,298 | B2 * | 9/2007 | Xu et al. | 568/816 |
| 8,034,983 | B2 * | 10/2011 | Du et al. | 568/816 |

* cited by examiner

*Primary Examiner* — Brian J Davis
(74) *Attorney, Agent, or Firm* — Marshall, Gerstein & Borun LLP

(57) ABSTRACT

Disclosed a process for preparing a xanthophyll crystal, comprising: dissolving the plant extract containing a xanthophyll ester in n-hexane, then filtering the mixture; adding acetone to the filtrate, filtering and collecting a filter cake; mixing the filter cake with soybean oil and ethanol uniformly; saponifying the mixed solution with alkaline aqueous solution; then adding an acidic solution thereto until the mixed solution becomes acidic, concentrating under reduced pressure to obtain a pasty substance; adding n-hexane to the pasty saponified product, standing still and then conducting a solid-liquid separation; washing the resulting solid substance with deionized water; adding a mixed solvent to the washed solid substance, dissolving it with stirring; and then adding n-hexane thereto and standing still to recrystallize. According to the application, organic solvents are used to treat the plant extract and remove non-xanthophyll ester compounds in order to improve the efficiency of the saponification reaction; the saponified solution is concentrated under acidic condition at reduced pressure, then extracted with an organic solvent for saving water; purifying a xanthophyll crystal with a mixed solvent in order to significantly increase the purity of a xanthophyll crystal and proportion of trans-xanthophyll.

13 Claims, 1 Drawing Sheet

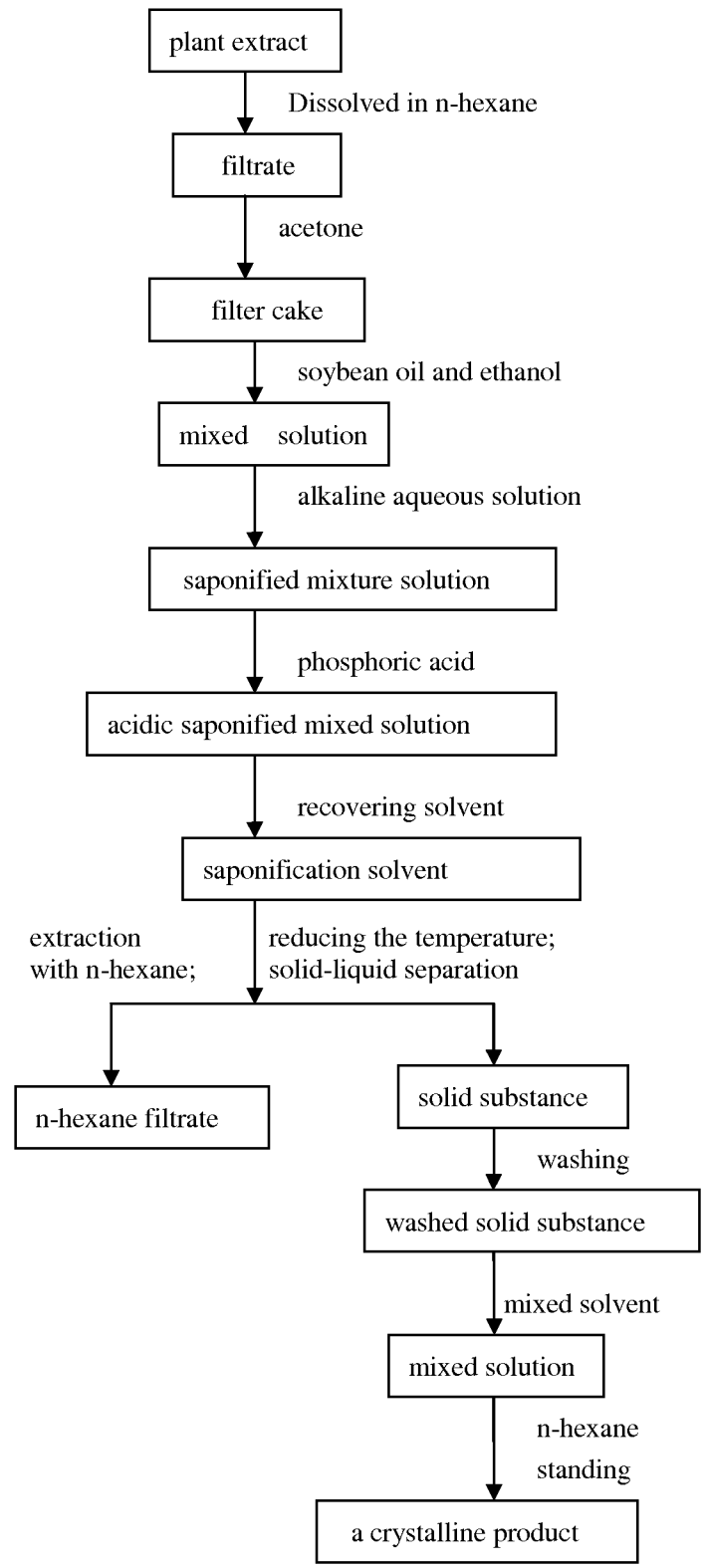

PROCESS FOR PREPARING XANTHOPHYLL CRYSTAL

TECHNICAL FIELD

This invention belongs to the field of health care product processing, particularly relates to a process for preparing a xanthophyll crystal.

BACKGROUND ART

Xanthophyll is a kind of carotenoid, which generally exists in flowers, leaves and fruits of plants as well as certain kinds of algae, especially exists in great quantity in marigold petals. Xanthophyll exists in plants in the form of a xanthophyll ester. Xanthophyll is generally obtained by saponifying an extract of plants in this industry. Recently, the biological functions of xanthophyll are drawn more attention. Xanthophyll has a strong effect of antioxidation and removes the harmful "free radicals" produced during the physiological metabolism process in human body. The "free radicals" are found to lead to lesions such as tissue damage, cell aging and the like. Early in 1995, xanthophyll is approved by FDA to be a supplement in food and drink. In the "list of new food additives and food flavorants (No.8 public announcement of the Ministry of Health of China in 2007)" announcement recently published in China, xanthophyll can be used in food as a colorant and nutrient supplement.

Since xanthophyll has a complex molecular structure, the industrial synthesis thereof is very difficult. However, natural xanthophyll in plants has a lot of advantages such as natural, nonhazardous, relatively low cost for extracting and purifying and being suitable for production in large scale. Although currently the production of xanthophyll resin achieves a large scale, most of the xanthophyll is produced in form of oleo-resin with impurities. Therefore, they are suitable to be used only as animal food but lack safety for using in human food as colorants and nutrient supplements.

U.S. Pat. No. 5,648,564 discloses a process for extracting a xanthophyll crystal from plants, wherein xanthophyll oleo-resin is dissolved with propylene glycol, alkali solution is added thereto for saponification at a higher temperature, water is added thereto and the crystals formed are filtered, and then the crystals are washed and dried to obtain a xanthophyll crystal. Since the propylene glycol used in the process has a higher boiling point, it is difficult to recover the solvent; and the final product has a purity of about 70% only and yield of about 60% only, which are relatively lower.

U.S. Pat. No. 6,743,953 discloses a process for separating and purifying xanthophyll from marigold oleoresin, wherein the oleoresin or xanthophyll ester is firstly saponified and then concentrated to obtain a concentrated solution, water is added thereto to dilute the concentrated solution, the resulting solution is extracted with ethyl acetate, and then concentrated to obtain a xanthophyll crystal. The xanthophyll obtained in this process has low purity, and large amount water used in the process is apt to cause environment pollution, and the yield of xanthophyll is relatively low.

U.S. Pat. No. 7,150,890 discloses a process for extracting xanthophyll from marigold petals, comprising the following steps: saponifying the dried petals; diluting the saponified liquid with water; adding metallic halide to the mixture in order to adjust the pH value of the mixture; filtering the pH-adjusted mixture to get a resultant solid; and then washing the resultant solid with a polar solvent to provide xanthophyll. Since the dried marigold petals are saponified directly in the process, the efficiency and yield of saponification is relatively low; the marigold flowers needs to be dried before extraction, and the time period for drying is too long and thus affects the production scale; using metallic halide to adjust the pH value leads to a extracting solution containing a large amount of metallic ions, which is apt to an environment pollution.

Process for preparing a xanthophyll crystal disclosed in China comprise: adding water or alcohol for crystallization after saponification, filtering the mixture to obtain coarse xanthophyll, and then recrystallizing the xanthophyll. A large amount of waste water is produced in the process, and the time period of the preparing process is prolonged, which is unfavorable for the stability of xanthophyll.

SUMMARY OF THE INVENTION

The object of this invention is to provide a process for preparing a xanthophyll crystal with high purity.

The detailed technical solutions are as follows without any limitation to the scope of the subject application:

The process for preparing a xanthophyll crystal, comprising the following steps:

a) dissolving a plant extract containing a xanthophyll ester in n-hexane, then filtering the mixture;

b) adding acetone to the filtrate, stand still, then filtering and collecting filter cake;

c) dissolving the filter cake with soybean oil and ethanol in order to obtain a mixed solution;

d) saponifying the mixed solution with an alkaline aqueous solution;

e) adding an acidic solution to the saponified solution until the mixed solution becomes acidic, and maintaining the temperature between 40-60° C. during the process of adding the acidic solution;

f) recovering the solvent and obtaining a pasty saponified product;

g) adding n-hexane to the pasty saponified product, maintaining the temperature between 40-60° C., stiring the mixture for 0.5-2 hours, reducing the temperature to 10-15° C., standing for 0.5-1.5 hours, and conducting a solid-liquid separation to obtain solid substance;

h) washing the resultant solid substance with deionized water at a temperature of 80-90° C.;

i) adding a mixed solvent of n-hexane, ethanol and acetone to the washed solid substance, and dissolve the solid substance with stirring;

j) adding n-hexane to the mixture solution obtained in step i), standing at a temperature between 0-10° C. to obtain crystalline product.

In an embodiment, the plant extract is extracted from one or more of corn, pumpkin, marigold, calendula, clove, peanut, alfalfa, medlar, cauliflower, broccoli, cabbage, carrot, spinach and fruits.

In an embodiment, the plant extract is marigold extract or oleoresin.

In an embodiment, in the step a), the mass ratio of the added n-hexane to the plant extract is 1-5:1. The purpose of dissolving the plant extract in n-hexane and filtering the mixture is to remove the non-liposoluble impurities from the extract.

In an embodiment, the volume of acetone added in the step b) is 5-20 times that of n-hexane added in step a), the standing temperature in the step b) is 0-10° C., and the standing time is 4-8 hours; the rate of adding acetone is 50-200 mL/min.

In an embodiment, in the step c), the mass ratio of the added soybean oil to filter cake is 1:1-5, the mass ratio of the ethanol to the filter cake is 1-5:1, stirring is needed after adding the soybean oil and ethanol, and the stirring temperature is maintained between 50-70° C.

In an embodiment, in the step d), the concentration of the alkali in the alkaline aqueous solution is 40-50% by mass; the time period of the saponification is 4-5 hours; the temperature of the saponification is 70-80° C., the mass ratio of the alkaline aqueous solution to soybean oil is 5:1-25, the time for adding the alkaline aqueous solution is 25-35 minutes.

In an embodiment, the acidic solution added in the step e) is food grade aqueous phosphoric acid solution, and the solution of soybean oil being acidic means the pH value of the solution is 1.0-6.9.

In an embodiment, recovering the solvent in the step f) is carried out by pressure-reduced method.

In an embodiment, the mass ratio of the n-hexane added in the step g) to the saponified product is 1-5:1; the solid-liquid separation is carried out by centrifugation or filtering.

In an embodiment, in the step i), in the mixed solvent the volume ratio of n-hexane:ethanol:acetone is 2:1:1; and the volume ratio of the mixed solvent to the solid substance is 1-20:1.

Wherein in the step j), n-hexane is added to the solution until the volume ratio of n-hexane:ethanol:acetone is 10:1:1, and the rate of adding the n-hexane is 10-100 mL/min; the standing time is 6-12 hours.

In an embodiment, after the step j), the process further comprises steps of separating the crystalline product, and then vacuum-drying or freeze-drying the crystalline product.

The advantageous effects of the invention lie in that:

Organic solvents are used to treat plant extract and remove non-xanthophyll ester compounds from plants, which can improve the efficiency of saponification reaction and reduce the difficulty for subsequent separation of a xanthophyll crystal; the saponified solution is concentrated under acidic condition at a reduced pressure, then extracted with organic solvent; which avoids diluting and washing the saponified solution with a large amount of deionized water, saves water and avoids environment pollution; using mixed solvent to purify the xanthophyll crystal can significantly increase the purity of a xanthophyll crystal and proportion of trans-xanthophylls.

The process according to the application is simple and efficient, and the yield and content of trans-xanthophylls are superior to the same of other prior processes, thus it is suitable for industrial production in large scale.

BRIEF DESCRIPTION OF THE DRAWING

FIG. 1 shows a flow chart of preparing a xanthophyll crystal according to the application.

BEST MODE OF EMBODIMENTS

The following Examples are intended to further illustrate the present application without limitation to the scope thereof.

All the percentage concentrations in the following examples refer to mass percent.

Example 1

1 kg of marigold extract containing xanthophyll ester (16.1% by mass based on xanthophyll) was dissolved in 2 L of n-hexane, well mixed, and then filtered at room temperature to obtain n-hexane filtrate. 20 L of acetone was added slowly to the filtrate with stirring and mixed well (in 2 hours), the mixture was filtered after standing for 5 hours at 5° C. to obtain 0.326 kg of filter cake. The filter cake was well mixed with 0.32 kg of soybean oil and 0.65 kg of ethanol at 50° C. to obtain a suspension, the suspension was heated to 70° C., then 0.33 kg of 45% aqueous potassium hydroxide solution was slowly added thereto, the dropping rate was adjusted to complete the dropping in 30 minutes at a constant rate, followed by keeping the same temperature and continuously stirring to conduct saponification reaction for 5 hours. After the saponification was finished, 0.095 L of 85% food grade aqueous phosphoric acid solution was slowly dropped to the saponified solution with stirring, and the pH value of the saponified solution was 6.24. The resulting acidic saponified solution was concentrated at 60° C. under a reduced pressure of −0.085 MPa to obtain a pasty substance.

1.8 L of n-hexane was added to the resulting pasty substance at 50° C. with stirring for 60 minutes, followed by reducing the temperature to 12° C. and standing for 60 minutes; solid content was collected by centrifugation, washed twice with 0.3 L of deionized water at 85° C., and filtered to obtain a coarse xanthophyll crystal; then 1.5 L of mixed solvent (n-hexane:ethanol:acetone=2:1:1) was added thereto to dissolve the coarse xanthophyll crystal, and 3 L of n-hexane was added to the above mixed solution with stirring (in 30 minutes); the mixture was recrystallized at 6° C. for 9 hours and then filtered to give a xanthophyll crystal, and the resulting crystals were dried in vacuum to yield 141.2 g of final product. The total content of carotenoid in the product reached 91.9%, the purity of all-trans-xanthophylls was 83.63% by HPLC, and the yield of the product reached 80.60%.

Example 2

1 kg of marigold extract containing xanthophyll ester (16.4% by mass based on xanthophyll) was dissolved in 2 L of n-hexane, well mixed, and then filtered at room temperature to obtain n-hexane filtrate. 20 L of acetone was added slowly to the filtrate with stirring in 1.8 hours and mixed well, the mixture was filtered after standing for 5 hours at 3° C. the mixture was filtered to obtain 0.331 kg of filter cake. The filter cake was well mixed with 0.33 kg of soybean oil and 0.68 kg of ethanol at 70° C. to obtain a suspension, then 0.33 kg of 45% aqueous potassium hydroxide solution was slowly added thereto, the dropping rate was adjusted to complete the dropping in 30 minutes at a constant rate, followed by keeping the same temperature and continuously stirring to conduct saponification reaction for 5 hours. After the saponification was finished, 0.095 L of 85% food grade aqueous phosphoric acid solution was slowly dropped to the saponified solution with stirring, and the pH value of the saponified solution was 6.11. The resulting acidic saponified solution was concentrated at 60° C. under a reduced pressure of −0.085 MPa to obtain a pasty substance.

2 L of n-hexane was added to the resulting pasty substance at 50° C. with stirring for 60 minutes, followed by reducing the temperature to 11° C. and standing for 60 minutes; solid content was collected by centrifugation, washed twice with 0.3 L of deionized water at 85° C., and filtered to obtain a coarse xanthophyll crystal; then 1.5 L of mixed solvent (n-hexane:ethanol:acetone=2:1:1) was added thereto to dissolve the coarse xanthophyll crystal, and 3 L of n-hexane was added to the above mixed solution with stirring in 60 minutes; the mixture was recrystallized at 5° C. for 10 hours and then filtered to obtain a xanthophyll crystal, and the resulting crystals were dried in vacuum to obtain 147.49 g l of final product. The total content of carotenoid in the product reached 90.5%, the purity of all-trans-xanthophylls was 83.63% by HPLC, and the yield of the product reached 81.39%.

Example 3

1 kg of marigold extract containing xanthophyll esters (16.3% by mass based on xanthophyll) was dissolved in 2 L of n-hexane, well mixed and then filtered at room temperature to obtain n-hexane filtrate, 20 L of acetone was added slowly to the filtrate with stirring in 2 hours and mixed well, the mixture was filtered after standing for 5 hours at 10° C., the mixture was filtered to obtain 0.32 kg of filter cake. The filter cake was mixed well with 0.32 kg of soybean oil and 0.66 kg of ethanol at 60° C. to obtain a suspension, the suspension was heated to 80° C., then 0.32 kg of 45% aqueous potassium hydroxide solution was slowly added thereto, the dropping rate was adjusted to complete the dropping in 30 minutes at a constant rate, followed by keeping the same temperature and continuously stirring to conduct saponification reaction for 4 hours. After the saponification was finished, 0.095 L of 85% food grade aqueous phosphoric acid solution was dropped slowly to the saponified solution with stirring, until the pH value of the saponified solution was 6.24. The resulting acidic saponified solution was concentrated at 60° C. under a reduced pressure of −0.085 MPa to obtain a pasty substance.

1.8 L of n-hexane was added to the resulting pasty substance at 50° C. with stirring for 60 minutes, followed by reducing the temperature to 15° C. and standing for 80 minutes; solid content was collected by centrifugation, washed twice with 0.3 L of deionized water at 85° C., and filtered to obtain a coarse xanthophyll crystal; then 1.5 L of mixed solvent (n-hexane:ethanol:acetone=2:1:1) was added thereto to dissolve the coarse xanthophyll crystal, and 3 L of n-hexane was added to the above mixed solution with stirring in 40 minutes; the mixture was recrystallized at 6° C. for 9 hours and then filtered to obtain the xanthophyll crystal, and the resulting crystals were dried in vacuum to obtain 140.2 g of final product. The total content of carotenoid in the product reached 91.6%, the purity of all-trans-xanthophylls was 83.63% by HPLC, and the yield of the product reached 80.60%.

Industrial Applicability

Organic solvents are used to treat plant extract and remove non-xanthophyll ester compounds in plants, which can improve the efficiency of saponification reaction and reduce the difficulty for subsequent separation of a xanthophyll crystal; the saponified solution is concentrated under acidic condition at a reduced pressure, then extracted with an organic solvent, which saves water; using mixed solvent to purify a xanthophyll crystal can significantly increase the purity of a xanthophyll crystal and proportion of trans-xanthophylls.

What is claimed is:

1. A process for preparing xanthophyll crystal, comprising the following steps:
   a) dissolving a plant extract containing a xanthophyll ester in n-hexane, then filtering the mixture;
   b) adding acetone to the filtrate, standing still, then filtering and collecting a filter cake;
   c) dissolving the filter cake with soybean oil and ethanol in order to obtain a mixed solution;
   d) saponifying the mixed solution with an alkaline aqueous solution;
   e) adding an acidic solution to the saponified solution until the mixed solution becomes acidic, and maintaining the temperature between 40-60° C. during the process of adding the acidic solution;
   f) recovering the solvent and obtaining a pasty saponified product;
   g) adding n-hexane to the pasty saponified product, maintaining the temperature between 40-60° C., stirring the mixture for 0.5-2 hours, reducing the temperature to 10-15° C., standing still for 0.5-1.5 hours, and conducting a solid-liquid separation to obtain solid substance;
   h) washing the resulting solid substance with deionized water at a temperature of 80-90° C.;
   i) adding a mixed solvent of n-hexane, ethanol and acetone to the washed solid substance, and dissolving the solid substance with stirring;
   j) adding n-hexane to the mixture solution obtained in step i), and standing still at a temperature between 0-10° C. to obtain crystalline product.

2. The process for preparing xanthophyll crystal according to claim 1, wherein the plant extract is extracted from one or more of corn, pumpkin, marigold, calendula, clove, peanut, alfalfa, medlar, cauliflower, broccoli, cabbage, carrot, spinach and fruits.

3. The process for preparing xanthophyll crystal according to claim 2, wherein the plant extract is marigold extract or marigold oleoresin.

4. The process for preparing xanthophyll crystal according to claim 1, wherein in the step a), the mass ratio of the added n-hexane to the plant extract is 1-5:1.

5. The process for preparing xanthophyll crystal according to claim 1, wherein the volume of acetone added in the step b) is 5-20 times that of n-hexane added in step a), the standing temperature in the step b) is 0-10° C., and the standing time is 4-8 hours; the rate of adding acetone is 50-200 mL/min.

6. The process for preparing xanthophyll crystal according to claim 1, wherein in the step c), the mass ratio of the added soybean oil to filter cake is 1:1-5, the mass ratio of the ethanol to the filter cake is 1-5:1, stirring is needed after adding the soybean oil and ethanol, and the stirring temperature is maintained between 50-70° C.

7. The process for preparing xanthophyll crystal according to claim 1, wherein in the step d), the concentration of the alkali in the alkaline aqueous solution is 40-50% by mass; the time period of the saponification is 4-5 hours; the temperature of the saponification is 70-80° C., the mass ratio of the alkaline aqueous solution to soybean oil is 5:1-25, the time for adding the alkaline aqueous solution is 25-35 minutes.

8. The process for preparing xanthophyll crystal according to claim 1, wherein the acidic solution added in the step e) is food grade aqueous phosphoric acid solution, the solution being acidic means the pH value of the solution is 1.0-6.9.

9. The process for preparing xanthophyll crystal according to claim 1, wherein recovering the solvent in the step f) is carried out by pressure-reduced method.

10. The process for preparing xanthophyll crystal according to claim 1, wherein the mass ratio of the n-hexane added in the step g) to the saponified product is 1-5:1; the solid-liquid separation is carried out by centrifugation or filtering.

11. The process for preparing xanthophyll crystal according to claim 1, wherein in the step i), in the mixed solvent the volume ratio of n-hexane: ethanol: acetone is 2:1:1; and the volume ratio of the mixed solvent to the solid substance is 1-20:1.

12. The process for preparing xanthophyll crystal according to claim 1, wherein in the step j), n-hexane is added to the solution until the volume ratio of n-hexane: ethanol: acetone is 10:1:1, and the rate of adding n-hexane is 10-100 mL/min; the standing time is 6-12 hours.

13. The process for preparing xanthophyll crystal according to claim 1, wherein after the step j), further comprising steps of separating the crystalline product, and then vacuum-drying or freeze-drying the crystalline product.

* * * * *